United States Patent [19]

Witte et al.

[11] Patent Number: 4,670,439

[45] Date of Patent: Jun. 2, 1987

[54] 2H-1-BENZOPYRAN-2-ONE DERIVATIVES, PROCESSES FOR THE PREPARATION THEREOF AND PHARMACEUTICAL COMPOSITIONS CONTAINING THEM

[75] Inventors: Ernst-Christian Witte, Mannheim; Peter Neubert, Weinheim; Androniki Roesch, Mannheim, all of Fed. Rep. of Germany

[73] Assignee: Boehringer Mannheim GmbH, Mannheim, Fed. Rep. of Germany

[21] Appl. No.: 755,496

[22] Filed: Jul. 16, 1985

[30] Foreign Application Priority Data

Jul. 28, 1984 [DE] Fed. Rep. of Germany ....... 3427985

[51] Int. Cl.[4] .................. A61K 31/495; C07D 405/12
[52] U.S. Cl. ..................................... 514/253; 544/376
[58] Field of Search ......................... 544/376; 514/253

[56] References Cited

U.S. PATENT DOCUMENTS

| | | | |
|---|---|---|---|
| 3,052,679 | 9/1962 | Cavallini et al. | 544/79 |
| 3,311,636 | 3/1967 | Moffett | 546/269 |
| 3,541,097 | 11/1970 | Beyerle et al. | 544/376 |
| 3,810,898 | 5/1974 | Witte et al. | 544/376 |

OTHER PUBLICATIONS

Brit. J. Pharmacol. (1960) 15,290 Versuchsanordnung zu Entersuchungen an der Bronchialmuskulatur von Heribert Konzett und Richard Rössler.
Tetrahedron Letters No. 15, pp. 1227-1228, 1976, Pergamon Press, Great Britain International Archives of Allergy and Applied Immunology.
Int. Arch. Allergy 45: 467-478 (1973).

*Primary Examiner*—Glennon H. Hollrah
*Assistant Examiner*—James H. Turnipseed
*Attorney, Agent, or Firm*—Felfe & Lynch

[57] ABSTRACT

The present invention provides 2H-1-benzopyran-2-one derivatives of the general formula:

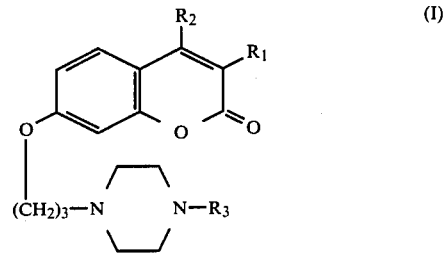

wherein either $R_1$ is a lower alkyl radical, optionally substituted by phenyl, which can be substituted by lower alkyl, lower alkoxy, hydroxyl or halogen, and $R_2$ is trifluoromethyl, cyano, hydroxymethyl, alkoxymethyl, acyloxymethyl, halogenomethyl, aminomethyl, mono- or dialkylaminomethyl, acyl, carboxyl, alkoxycarbonyl or carbamoyl, which can be mono- or disubstituted by lower alkyl; or $R_1$ is trifluoromethyl, cyano, hydroxymethyl, alkoxymethyl, acyloxymethyl, halogenomethyl, aminomethyl, mono- or dialkylaminomethyl, acyl, carboxyl, alkoxycarbonyl or carbamoyl, which can be mono- or disubstituted by lower alkyl, and $R_2$ is a lower alkyl radical, optionally substituted by phenyl, which can be substituted by lower alkyl, lower alkoxy, hydroxyl or halogen, and $R_3$ is a phenyl or benzyl radical which can be substituted by lower alkyl, lower alkoxy, hydroxyl or halogen; and the pharmacologically acceptable salts thereof.

The present invention also provides processes for the preparation of these 2H-1-benzopyran-2-one derivatives and pharmaceutical compositions containing them.

17 Claims, No Drawings

2H-1-BENZOPYRAN-2-ONE DERIVATIVES, PROCESSES FOR THE PREPARATION THEREOF AND PHARMACEUTICAL COMPOSITIONS CONTAINING THEM

The present invention is concerned with new 2H-1-benzopyran-2-one derivatives, processes for the preparation thereof and pharmaceutical compositions containing them.

The new 2H-1-benzopyran-2-one derivatives according to the present invention are compounds of the general formula:

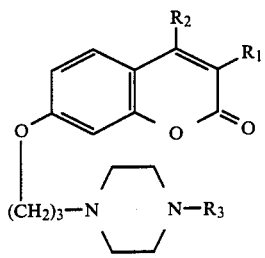

(I)

wherein either $R_1$ is a lower alkyl radical, optionally substituted by phenyl, which can be substituted by lower alkyl, lower alkoxy, hydroxyl or halogen, and $R_2$ is trifluoromethyl, cyano, hydroxymethyl, alkoxymethyl, acyloxymethyl, halogenomethyl, aminomethyl, mono- or dialkylaminomethyl, acyl, carboxyl, alkoxycarbonyl or carbamoyl, which can be mono- or disubstituted by lower alkyl; or $R_1$ is trifluoromethyl, cyano, hydroxymethyl, alkoxymethyl, acyloxymethyl, halogenomethyl, aminomethyl, mono- or dialkylaminomethyl, acyl, carboxyl, alkoxycarbonyl or carbamoyl, which can be mono- or disubstituted by lower alkyl, and $R_2$ is a lower alkyl radical, optionally substituted by phenyl, which can by substituted by lower alky, lower alkoxy, hydroxyl or halogen; and $R_3$ is a phenyl or benzyl radical which can be substituted by lower alkyl, lower alkoxy, hydroxyl or halogen; as well as the pharmacologically acceptable salts thereof.

The lower alkyl radicals $R_1$ and $R_2$, as well as the substituents in the phenyl radicals, contain 1–6 and preferably 1–4 carbon atoms, methyl and ethyl radicals being preferred. Lower alkoxy substituents contain 1–6 and preferably 1–4 carbon atoms, methoxy and ethoxy radicals being preferred.

Acyloxymethyl radicals are preferably benzoyloxymethyl, pivaloyloxymethyl or acetoxymethyl radicals.

Acyl radicals contain 1–6 carbon atoms, the formyl, acetyl and propionyl radicals being preferred.

In all cases, halogen means fluorine, chlorine or bromine, chlorine being preferred.

Preferred substituents on amino groups and also of amides include methyl and ethyl radicals.

The alkoxycarbonyl radicals are preferably methoxycarbonyl or ethoxycarbonyl radicals.

After oral or inhalatory administration, the new compounds have a strongly inhibiting action on allergic reactions of the skin and bronchi. They suppress the liberation of histamine caused by antigens or anti-IgE and other mediators, auch as proteinases from various cells, for example human leukocytes. Furthermore, the new compounds have antagonistic properties towards mediators and especially towards histamine. On the basis of these properties, the new compounds can also be regarded as being inhibitors of inflammation.

The new compounds according to the present invention can be prepared in that either (a) a compound of the general formula:

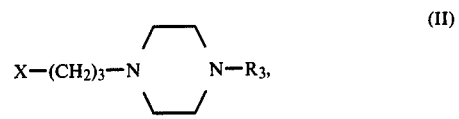

(II)

in which $R_3$ has the above-given meaning and X is a reactive group, is condensed in known manner with a compound of the general formula:

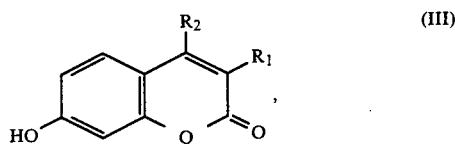

(III)

in which $R_1$ and $R_2$ have the above-given meanings; or (b) a compound of the general formula:

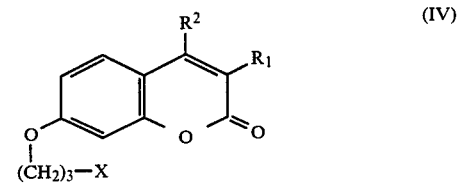

(IV)

in which $R_1$, $R_2$ and X have the above-given meanings, is condensed in known manner with a compound of the general formula:

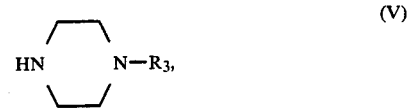

(V)

in which $R_3$ has the above-given meaning; or (c) when $R_3$ is an optionally substituted benzyl radical, a compound of the general formula:

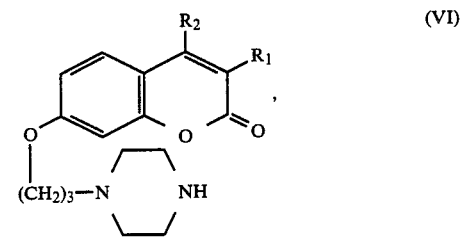

(VI)

in which $R_1$ and $R_2$ have the above-given meanings, is condensed in known manner with a compound of the general formula X-$R_3$, in which $R_3$ and X have the above-given meanings;

whereupon the product obtained is, if desired, converted into a physiologically acceptable salt.

A preferred reactive group X is halogen. On the other hand, the compounds of general formula (I) can also be prepared by condensing a compound of the general formula:

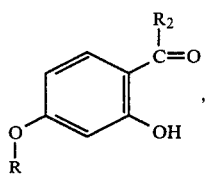

in which R is a hydrogen atom, a protective group which is easily removed, for example a tetrahydropyranyl, benzyl or methyl radical or a radical of the general formula:

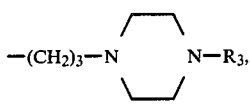

in which $R_3$ has the above-given meaning, with a compound of the general formula:

in which $R_6$ is a carboxyl function, an ester or nitrile group or the function $-CO-O-CO-CH_2R_1$, the protective group is possibly removed and the resulting phenol reacted according to method (a) or (b).

Compounds of general formula (I), in which $R_1$ is an electronegative group, for example a nitrile function, and $R_2$ is a lower alkyl radical or an optionally substituted benzyl radical, can be prepared from compounds of the general formula:

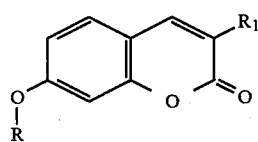

in which R has the above-given meaning, by reaction with a diazoalkane or with phenyldiazomethane optionally substituted in the aromatic nucleus. It is thus an alkylation or benzylation in the 4-position of the coumarin ring.

Compounds of general formula (I) can also be obtained by changing the substituents $R_1$ and/or $R_2$. Such changes can be brought about by:

1. oxidation or reduction reactions,
2. hydrolysis or alcoholysis reactions,
3. alkylation or acylation reactions.

Examples of such changes include the reduction of a carboxyl function to a hydroxymethyl radical or the oxidation of a hydroxymethyl radical to a carboxyl function but also, for example, the oxidation of a methyl radical by means of N-halogenoimides to a halogenomethyl radical. An example of (2) is the hydrolysis of a nitrile function to a carbonamide and further to a carboxylic acid but also the alcoholysis of a nitrile group to a carboxylic acid ester radical.

As examples of alkylations and acylations according to (3), there may be mentioned the etherification of a hydroxymethyl radical by means of alkylating agents or the formation of a carbonamide by acylation of an aminomethyl function. The reactions mentioned above under (a) to (c) are all carried out by known processes. Thus, for example, U.S. Pat. No. 3,311,636 describes the reaction of hydroxysalicylaldehydes and U.S. Pat. No. 3,053,679 the reaction of 4-methyl-5,7-dihydroxycoumarins with aminoalkyl halides in the presence of alkali metal hydroxides.

In order to take up the acid HX liberated in the case of reactions (a) to (c), it is preferable to operate in the presence of acid-binding agents, for example of alkali metal or alkaline earth metal carbonates, alkali metal hydrogen carbonates, alkali metal or alkaline earth metal hydroxides or alkali metal alcoholates. For aminoalkylations, tertiary amines can also be used as acid acceptors.

The reaction medium used is preferably an inert solvent, for example acetone, butanone, dimethylformamide or a lower alcohol, and for aminoalkylations cyclic ethers, for example tetrahydrofuran or dioxan, can also be used.

For the known ring closure reactions, there can be used not only acidic but also alkaline condensation agents. As acidic condensation agents, there may be mentioned, for example, gaseous hydrogen chloride, optionally in the presence of a Lewis acid, such as zinc chloride. As basic condensation agents, there may be mentioned, for example, alkali metal and alkaline earth metal hydroxides, alkali metal alcoholates and alkali metal salts of carboxylic acids.

The condensation reactions are preferably carried out in a liquid reaction medium, for example glacial acetic acid (for acidic condensations) or in water or alcohols (for basic condensations). However, in individual cases, such condensations are also carried out by melting together the reaction components at temperatures of about 220° C., the addition of catalytic amounts of an adjuvant, for example sodium acetate, being necessary.

The alkylation or benzylation with diazoalkanes or with phenyldiazomethanes was first described by Clinging, Dean, Houghton and Park in Tetrahedron Letters, 15, 1227–1228/1976. The reaction takes place at temperatures of from 0° to 20° C. in a mixture of tetrahydrofuran and diethyl ether.

For the indicated conversions of functional groups $R_1$ and $R_2$ into other functional groups, there are used standard processes of organic chemistry.

It is obvious that alkylatable functional groups $R_1$ or $R_2$ must first be blocked by protective groups when it is desired to carry out alkylations on the hydroxycoumarin (process (a)) or on the piperazine ring (processes (b) and (c)). After the reaction has taken place according to (a), (b) or (c), the protective group is again removed.

For the preparation of salts with pharmacologically acceptable organic or inorganic acids, for example hydrochloric acid, sulphuric acid, phosphoric acid, lactic acid, citric acid or alkylsulphonic acids, the substances can be reacted with the appropriate acids.

For the preparation of pharmaceuticals, the compounds of general formula (I) are mixed with appropriate pharmaceutical carrier substances, aroma, flavouring and colouring materials and formed, for example, into tablets or dragees or, with the addition of appropriate adjuvants, suspended or dissolved in water or in an oil, for example olive oil.

The compounds of general formula (I) can be administered orally or parenterally in liquid or solid form. As injection medium, it is preferred to use water which contains the stabilising agents, solubilising agents and- /or buffers usual in the case of injection solutions. Such additives are, for example, tartrate and borate buffers, ethanol, dimethyl sulphoxide, complex forming agents (such as ethylenediamine-tetraacetic acid), high molecular weight polymers (such as liquid polyethylene oxide) for viscosity regulation and polyethylene derivatives of sorbitan anhydrides.

Solid carrier materials include, for example, starch, lactose, mannitol, methyl cellulose, talc, highly dispersed silicic acid and high molecular weight polymers (such as polyethylene glycols).

Compositions suitable for oral administration can, if desired, contain flavouring and sweetening agents. For external use, the compounds (I) according to the present invention can also be employed in the form of powders and salves. For this purpose, they are mixed, for example, with powdered. physiologically compatible diluents or with conventional salve bases.

The dosage administered depends upon the age, the state of health and the weight of the recipient, the extent of the disease, the nature of possibly simultaneously carried out further treatments, the frequency of the treatments and the nature of the desired action. Usually, the dialy dosage of the active compound is from 0.1 to 50 mg./kg. body weight. Normally, from 0.5 to 40 and preferably from 1.0 to 20 mg./kg./day in one or more applications per day are effective in order to obtain the desired results.

The compounds can be used as such or they can be converted to salts with pharmacologically acceptable acids. They can be administered to patients orally, as pills, tablets, capsules, powders and the like. The preferred form of oral administration is a tablet containing 10 to 300 mg of active compound, which is the range of typical daily dosages. The preferred content or dosage is 30 to 100 mg.

The compounds can also be administered parenterally. Injection solutions (normally aqueous) containing the active compound in an amount of 0.05 to 50 mg/ml of injection solution are administered.

EXPERIMENTAL PROCEDURE

The superior activity of the novel compounds is shown by comparing the inhibition of antigen induced bronchospasms in passively sensitized guinea pigs. Specifically, tests were run as follows:

Preparation of Antiserum:

The antigen is twice recrystallized egg albumin. Equal volumes of saline solution of antigen (5 mg/ml) and Freund's complete adjuvant were emulsified and 0.15 ml injected into each hind foot of adult male guinea pigs.

(Davies and Johnson: *Int. Arch. Allergy*, 41, 648–654, 1971).

The animals were bled and the pooled serum stored at −20° C.

Passive Sensitization:

Injections of 0.5 ml antiserum of 1:50 dilution were given i.v. 24-48 hrs. before challenge.

Guinea pigs were anaesthetized with pentobarbitone sodium 40 mg/kg i.p.). Cannulae were tied into the trachea and the jugular vein and the lung inflated with a pump at a rate of 72 strokes/min. and a constant stroke volume of 6-8 ml.

Bronchospasm, provoked by injecting ovalbumim i.v. was measured as described by Konzett Rössler (Versuchsanordnung zu Untersuchungen an der Bronchialmuskulat Naunyn-Schmiedebergs Arch. exp. Path.

Pharmak. 195, 71–74, 1940), and modified by Collier and James (Collier, H. O. J., J. A. Holgate, M. Schachter: The Bronchoconstrictor Action of Bradykinin in the Guinea-Pig, *Brit. J. Pharmacol.*, 15, 290, 1960).

Drugs were applied p.o. 75 minutes before antigen. For calculation the following formula was used:

$$\% \text{ Bronchospasm } \frac{b-a}{m-a} \times 100$$

b = Bronchospasm after antigen injection, measured in mm from tracing m = Maximum height of tracing in mm with arm of the trachea-cannula clamped a = pre-injection height of the tracing in mm Percent (%) inhibition of bronchospasm was calculated by comparing control groups with drug pretreated groups 3 minutes after antigen application.

| Inhibition of antigen induced bronchospasm (BrSp) in passively sensitized guinea pig | | |
|---|---|---|
| Example | Dose (mg/kg) | Inhibition of BrSp (%) |
| 3 | 0.1 | 88 |
| 7a | 0.1 | 23 |
| 10 | 0.1 | 83 |
| 9 | 0.75 | 37 |
| 6 | 0.1 | 35 |
| A | 0.2 | 3 |

A = 1-(4-chlorobenzyl)-4-[3-(3,4-dimethyl-cumarin-7-yl-oxy)-propyl]-piperazine

Apart from the compounds mentioned in the Examples, the following conpounds are also preferred according to the present invention:

1. 3-bromomethyl-7-{3-{4-[(4-chlorophenyl)-methyl]-7-piperazinyl}-propoxy}-4-methyl-2H-1-benzopyran-2-one
2. 3-aminomethyl-7-{3-{4-[(4-chlorophenyl)-methyl]-1-piperazinyl}-propoxy}-4-methyl-2H-1-benzopyran-2-one
3. 7-3-{4-[(4-chlorophenyl)-methyl]-1-piperazinyl}-{propoxy}-3-diethylaminomethyl-4-methyl-2H-1-benzopyran-2-one
4. 7-{3-{4-[(4-chlorophenyl)-methyl9 -1-piperazinyl}-propoxy}-3-methoxymethyl-4-methyl-2H-1-benzopyran-2-one
5. 7-{3-{4-[(4-chlorophenyl)-methyl]-1-piperazinyl}-propoxy}-4-methyl-3-trifluoromethyl-2H-1-benzopyran-2-one
6. 7-{3-{4-[(4-chlorophenyl)-methyl]-1-piperazinyl}-propoxy}-3-cyano-4-phenylmethyl-2H-1-benzopyran-2-one
7. 7-{3-{4-[(4-chlorophenyl)-methyl]-1-piperazinyl}-propoxy}-4-phenylmethyl-2H-1-benzopyran-2-one-3-carboxylic acid as well as its ethyl ester, amide and diethylamide
8. 4-[(4-chlorophenyl)-methyl]-7-{3-{4-[(4-chlorophenyl)-methyl]-1-piperazinyl}-propoxy}-3-cyano-2H-1-benzopyran-2-one
9. 4-[(4-chlorophenyl)-methyl]-7-{3-{4-[(4-chlorophenyl)-methyl]-1-piperazinyl}-propoxy}-2H-1-benzopyran-2-one-3carboxylic acid as well as its ethyl ester, amide and diethylamide
10. 7-{3-{4-[(4-chlorophenyl)-methyl]-1-piperazinyl}-propoxy}-3-phenylmethyl-2H-1-benzopyran-2-one-4-carboxylic acid as well as its amide 11. 7-{3-{4-[(4-chlorophenyl)-methyl]-1-piperazinyl}-propoxy}-4-hydroxymethyl-3-phenylmethyl-2H-1-benzopyran-2-one
12. 7-{3-{4-[(4-chlorophenyl)-methyl]-1-piperazinyl}-propoxy}-4-methoxymethyl-3-phenylmethyl-2H-1-benzopyran-2-one
13. 3-[(4-chlorophenyl)-methyl]-7-{3-{4-[(4-chlorophenyl)-methyl]-1-piperazinyl}-propoxy}-2H-1-benzopyran-2-one-4-carboxylic acid as well as its ethyl ester and amide
14. 3-[(4chlorophenyl)-methyl]-7-{3-{4-[(4-chlorophenyl)-methyl]-1-piperazinyl}-propoxy}-4-hydroxymethyl-2H-1-benzopyran-2-one
15. 3-[(4-chlorophenyl)-methyl]-7-{3-{4-[(4-chlorophenyl)-methyl]-1-piperazinyl}-propoxy}-4-methoxymethyl-2H-1-benzopyran-2-one The following Examples are given for the purpose illustrating the present invention: EXAMPLE 1

Ethyl 7-{3-{4-[(4-chlorophenyl)-methyl]-1-piperazinyl}-propoxy}3-methyl-2H-1-benzopyran-2-one-4-carboxylate A suspension of 10.5 g. (42 mmol) ethyl 7-hydroxy-3-methyl-2H-1-benzopyran-2-one-4-carboxylate, 230 ml. butanone and 18.0 g. (130 mmol) pulverised, anhydrous potassium carbonate is maintained at reflux temperature for 2 hours, then cooled, a spatula tip of potassium iodide added thereto and then a solution of 100 ml. butanone and 13.3 g. (46 mmol) 3-{4-[(4-chlorophenyl)-methyl]- 1-piperazinyl}-propyl chloride added dropwise thereto. The reaction mixture is subsequently maintained at reflux temperature for 16 hours. It is then cooled somewhat, suction filtered while still warm and the filtrate then evaporated. The residue is dissolved in diethyl ether and the ethereal solution is treated with active charcoal, filtered and again evaporated. The crude base thus obtained is dissolved in warm ethanol, double the molar amount of maleic acid is added thereto, cooled and the salt formed is filtered off with suction and recrystallised from ethanol. There are obtained 27.0 g. (87% of theory) of the dimaleate; m.p. 175°–176° C. The free base, after recrystallisation from ethanol, melts at 75° C.

The following compound is prepared in an analogous manner:
ethyl 7-{3-{4-[(4-chlorophenyl)-methyl]-1-piperazinyl}-propoxy}-3-phenylmethyl-2H-1-benzopyran-2-one-4-carboxylate from ethyl 7-hydroxy-3-phenylmethyl-2H-1-benzopyran-2-one-4-carboxylate and 3-{4-[(4-chlorophenyl)-methyl]-1-piperazinyl}-propyl chloride.

EXAMPLE 2

7-{3-{4-[(4-chlorophenyl)-methyl]-1-piperazinyl}-propoxy}-3-methyl-2H-1-benzopyran-2-one-4-carboxylic acid A mixture of 13.5 g. (27 mmol) of the ethyl ester described in Example 1 (in the form of the free base), 50 ml. ethanol and 25 ml. 2N aqueous sodium hydroxide solution is stirred for 3 hours at ambient temperature, then acidified with concentrated hydrochloric acid and evaporated somewhat in a vacuum. The reaction mixture is then suction filtered and the crude product obtained is recrystallised from very dilute hydrochloric acid. The yield is 11.8 g. (80% of theory) of dihydrochloride; m.p. 238°–241° C. (decomp.).

EXAMPLE 3

7-{3-{4-[(4-Chlorophenyl)-methyl]-1-piperazinyl}-propoxy}-4-hydroxymethyl-3-methyl-2H-1-benzopyran-2-one A mixture of 1.7 g. (3 mmol) 7-{3-{4-[(4-chlorophenyl)-methyl]-1-piperazinyl}-propoxy}-3-methyl-2H-1-benzopyran-2-one-4-carboxylic acid dihydrochloride, 0.98 g. (8.7 mmol) anhydrous triethylamine and 20 ml. anhydrous tetrahydrofuran is stirred for 30 minutes at ambient temperature. The reaction mixture is then cooled and a solution of 0.38 g. (3.5 mmol) ethyl chloroformate and 10 ml. anhydrous tetrahydrofuran added dropwise thereto at an internal temperature of from −5° to −10° C. The reaction mixture is allowed to react for 30 minutes at −5° C. and subsequently the precipitated triethylamine hydrochloride is filtered off with suction with the exclusion of moisture. The filtrate is added dropwise at +10° C. to a suspension of 93 mg. (2.5 mmol) sodium borohydride and 1.5 ml. water. The reaction mixture is now stirred for 2 hours at ambient temperature, subsequently evaporated in a vacuum and the residue mixed with a mixture of ice and sodium hydrogen carbonate solution. It is then extracted several times with ethyl acetate and the extract is dried with anhydrous sodium sulphate and finally evaporated. After recrystallisation from ethanol, there is obtained 0.84 g. (59% of theory) of base; m.p. 135° C.; dihydrochloride m.p. 241° C., after recrystallisation from methanol.

EXAMPLE 4

7-{3-{4-[(4-Chlorophenyl)-methyl]-1-piperazinyl}-propoxy}-3-methyl-4-trifluoromethyl-2H-1-benzopyran-2-one 1. A mixture of 18.1 g. (87.8 mmol) 1-(2,4-dihydroxyphenyl)-2,2,2-trifluoroethanone, 23.5 g. (180.6 mmol) propionic acid anhydride and 6.0 g. (62.5 mmol) sodium propionate is heated for 8 hours at 190° C., then cooled, dissolved in ethanol and mixed with a concentrated aqueous solution of ammonia until the reaction is strongly alkaline. After standing for 30 minutes, the reaction mixture is acidified with 2N hydrochloric acid and extracted with methylene chloride. The extract is dried with anhydrous sodium sulphate, evaporated and the residue is recrystallised from toluene. Yield: 9.9 g. (46% of theory) 7-hydroxy-3-methyl-4-trifluoromethyl-2H-1-benzopyran-2-one; m.p. 161°–162° C.

2. The title compound is obtained by reacting 7-hydroxy-3-methyl-4-trifluoromethyl-2H-1-benzopyran-2-one with 3-{4-[(4-chlorophenyl)-methyl]-1-piperazinyl}-propyl chloride in a manner analogous to that described in Example 1. Yield: 12.4 g. (54% of theory) of dihydrochloride; m.p. 260° C. (decomp.).

EXAMPLE 5

The following compounds are prepared in a manner analogous to that described in Example 1:

From ethyl 7-hydroxy-4-methyl-2H-1-benzopyran-2-one-3-carboxylate and
(a) 3-{4-[(4-chlorophenyl)-methyl]-1-piperazinyl}-propyl chloride, the compound ethyl 7-{3-{4-[(4-chlorophenyl)-methyl]-1-piperazinyl}-propoxy}-4-methyl-2H-1-benzopyran-2-one-3-carboxylate; yield: 83% of theory of dihydrochloride; m.p. 245° C. (decomp.) after recrystallisation from aqueous ethanol (b) 3-{4-[(2-chlorophenyl)-methyl]-1-piperazinyl}-propyl chloride, the compound ethyl 7-{3-{4-[(2-chlorophenyl)-methyl]-1-piperazinyl}-propoxy}-4-methyl-2H-1-benzopyran-2-one-3-carboxylate
(c) 3-(4-phenyl-1-piperazinyl)-propyl chloride, the compound ethyl 4-methyl-7-{3-[4-phenyl-1-piperazinyl]-propoxy} -2H-1-benzopyran-2-one-3-carboxylate.

EXAMPLE 6

In a manner analogous to that described in Example 1, there is prepared 7-{3-{4-[(4-chlorophenyl)-methyl]-1-piperazinyl}-propoxy}-3-cyano-4-methyl-2H-1-benzopyran-2-one by the reaction of 3-cyano-7-hydroxy-4-methyl-2H-1-benzopyran-2-one with 3-{4-[(4-chlorophenyl)-phenyl)-methyl]-1-piperazinyl}-propyl chloride; yield: 61% of theory of dimaleate; m.p. 170°–171° C. (decomp.), recrystallised from methanol.

EXAMPLE 7

The following compounds are prepared by hydrolysis of the corresponding ethyl esters in a manner analogous to that described in Example 2:
(a) 7-{3-{4-[(4-chlorophenyl)-methyl]-1-piperazinyl}-propoxy}-4-methyl-2H-1-benzopyran-2-one-3-carboxylic acid; yield: 70% of theory of dihydrochloride monohydrate; m.p. 252°–253° C. (decomp.), recrystallised from aqueous ethanol
(b) 7-{3-{4-[(2-chlorophenyl)-methyl]-1-piperazinyl}-propoxy}-4-methyl-2H-1-benzopyran-2-one-3-carboxylic acid
(c) 4-methyl-7-[3-(4-phenyl-1-piperazinyl)-propoxy]-2H-1-benzopyran-2-one-3-carboxylic acid
(d) 7-{3-{4-[(4-chlorophenyl)-methyl]-1-piperazinyl}-propoxy}-4-phenylmethyl-2H-1-benzopyran-2-one-3-carboxylic acid as dihydrochloride monohydrate; m.p. 243°–246° C.; yield: 69% of theory.

EXAMPLE 8

7-{3-{4-[(4-Chlorophenyl)-methyl]-1-piperazinyl} propoxy}-4-methyl-2H-1-benzopyran-2-one-3-carboxylic acid amide 1 A mixture of 12.0 g. (22 mmol) 7-{3-{4-[(4-chlorophenyl)-methyl]-1-piperazinyl}-propoxy}-4-methyl-2H-1-benzopyran-2-one-3-carboxylic acid dihydrochloride, 100 ml. anhydrous chloroform and 36 g. (0.3 mol) thionyl chloride is stirred for 4 hours at 60° C., a thick crystalline slurry thereby being formed. After standing overnight, the reaction mixture is evaporated to dryness and the residue stirred up with anhydrous diethyl ether. After suction filtration and drying, there are obtained 12.0 g. (97% of theory) 7-{3-{4-[(4-chlorophenyl)-methyl]-1-piperazinyl}-propoxy}-4-methyl-2H-1-benzopyran-2-one-3-carboxylic acid chloride in the form of the dihydrochloride; m.p. 257°–259° C.

2. The title compound is obtained by slowly introducing the acid chloride into liquid ammonia, evaporating the ammonia and working up the residue. This is treated with a dilute aqueous solution of ammonia. It is then extracted with methylene chloride and the organic phase is washed with water and dried with anhydrous sodium sulphate. The methylene chloride is then evaporated, the residue is dissolved in diethyl ether and the dihydrochloride precipitated out by the addition of hydrogen chloride-containing diethyl ether. After recrystallisation from aqueous methanol, there is obtained the pure dihydrochloride in a yield of 64% of theory; m.p. 256°–258° C.

According to a variant of this process, instead of introducing the acid chloride into liquid ammonia, it is introduced into an ice-cold mixture of dioxan and concentrated aqueous ammonia solution and then worked up accordingly.

According to this variant, there is prepared 7-{3-{4-[(4-chlorophenyl)-methyl]-1-piperazinyl}-propoxy}-3-methyl-2H-1-benzopyran-2-one-4-carboxylic acid amide.

EXAMPLE 9

7-{3-{4-[(4-Chlorophenyl)-methyl]-1-piperazinyl}-propoxy}-4-methyl-2H-1-benzopyran-2-one-3-carboxylic acid diethylamide 6.0 g. (107 mmol) of the acid chloride obtained according to Example 8 (a) (in the form of the dihydrochloride) are added portionwise, while stirring, to an ice-cold solution of 7.8 g. (107 mmol) diethylamine in 30 ml. anhydrous tetrahydrofuran and stirring is continued for a further 2 hours. The reaction mixture is then evaporated, the residue is dissolved in ethanol and the dihydrochloride precipitated out by the addition of hydrogen chloride-containing diethyl ether. After suction filtration and recrystallisation from methanol, which contains a few percent of 2N hydrochloric acid, there are obtained 4.65 g. (73% of theory) of the diethylamide dihydrochloride; m.p. 227°–229° C.

In an analogous manner, from the appropriate acid chloride and diethylamine, there is obtained 7-{3-{4-[(4-chlorophenyl)-methyl]-1-piperazinyl}-propoxy}-4-phenylmethyl-2H-1-benzopyran-2-one-3-carboxylic acid diethylamide as the dihydrochloride; yield 57% of theory; m.p. 228°–230° C.

EXAMPLE 10

7-{3-{4-[(4-Chlorophenyl)-methyl]-1-piperazinyl}-propoxy}-3-hydroxymethyl-4-methyl-2H-1-benzopyran-2-one 5.0 g. (9 mmol) of the acid chloride obtained according to Example 8 (a) (in the form of the dihydrochloride) are added portionwise at a temperature of from 0° to +5° C., while stirring vigorously, to a suspension of 5 g. (130 mmol) sodium borohydride in 50 ml. water, a strong foam formation thereby taking place. Subsequently, the reaction mixture is stirred for 1 hour at 0° C. and for a further hour at ambient temperature and then adjusted to pH 4 with dilute hydrochloric acid. The precipitated greasy product is treated with an aqueous solution of sodium hydrogen carbonate. It is then extracted with methylene chloride and the organic phase is dried with anhydrous sodium sulphate and evaporated. After column chromatography (silica gel; methylene chloride/methanol 19/1 v/v), there are obtained 2.1 g. (52% of theory) of the free base, the dihydrochloride of which melts at 9 256° C., after recrystallisation from aqueous ethanol.

In an analogous manner, the following compounds are obtained from the appropriate acid chlorides:
(a) 7-{3-{4-[(4-chlorophenyl)-methyl]-1-piperazinyl}-propoxy}-3-hydroxymethyl-4-phenylmethyl-2H-1-benzopyran-2-one; and
(b) 4-[(4-chlorophenyl)-methyl]-7-{3-{4-[(4-chlorophenyl)-methyl]-1-piperazinyl}-propoxy}-3-hydroxymethyl-2H-1-benzopyran-2-one.

EXAMPLE 11

Ethyl 7-{3-{4-[(4-chlorophenyl)-methyl]-1-piperazinyl}-propoxy}-4-phenylmethyl-2H-1-benzopyran-2-one-3-carboxylate (a) A mixture of 20.0 g. (63 mmol) 1-(2-hydroxy-4-phenylmethoxyphenyl)-2-phenylethanone, 52.8 g. (0.33 mmol) diethyl methane-dicarboxylate and 6.0 g. (50 mmol) potassium tert.-butoxide is stirred for 30 minutes at 170° C., then cooled and dissolved in toluene. After separation of insoluble material and treatment with silica gel, the solution is evaporated. The crystalline residue is washed with ligroin and then recrystallised from cyclohexane or ethyl acetate. There are obtained 21.0 g. (81% of theory) ethyl 4-phenylmethyl-7-phenylmethoxy-2H-1-benzopyran-2-one-3-carboxylate; m.p. 117°–118° C.

(b) 20.0 g. (48.3 mmol) of the product obtained according to (a) above are dissolved in 200 ml. ethanol and 400 ml. anhydrous tetrahydrofuran, about 1 g. 5% palladium-charcoal is added thereto and hydrogenation is carried out for 24 hours in a shaking vessel at normal pressure. After filtering off the catalyst with suction, the filtrate is evaporated, the crystalline residue is dissolved in hot ethyl acetate and insoluble material is separated off. The filtrate is then mixed with ligroin and the precipitated crystals are filtered off with suction and recrystallised from toluene. There are obtained 8.3 g. (53% of theory) ethyl 7-hydroxy-4-phenylmethyl-2H-1-benzopyran-2-one-3-carboxylate; m.p. 150°–152° C.

(c) By reacting the product obtained in (b) above with 3-{4-[(4-chlorophenyl)-methyl]-1-piperazinyl}-propyl chloride in a manner analogous to that described in Example 1, the title compound is obtained, in a yield of 73% of theory, in the form of the dihydrochloride; m.p. 220°–223° C., after recrystallisation from aqueous ethanol.

EXAMPLE 12

7-{3-{4-[(4-Chlorophenyl)-methyl]-1-piperazinyl}-propoxy}-4-[(4-chlorophenyl)-methyl]-2H-1-benzopyran-2-one-3-carboxylic acid (a) A mixture of 20.0 g. (76 mmol) 1-(2,4-dihydrophenyl)-2-(4-chlorophenyl)-ethanone, 105.6 g. (0.66 mol) diethyl methane-dicarboxylate and 10 g. (89 mmol) potassium tert.-butoxide is heated for about 10 minutes to about 210° C. and excess diethyl methanedicarboxylate is then distilled off, a deep red crystalline slurry thereby being obtained. After distilling off residual diethyl methanedicarboxylate in a vacuum, the residue is mixed with dilute hydrochloric acid, ethyl acetate is added thereto and the mixture then stirred until the crystals have dissolved. The organic phase is then separated off, dried with anhydrous sodium sulphate and evaporated. The residue is chromatographed by means of silica gel/toluene until all impurities have left the column and the desired product is then eluted from the column with diethyl ether. After evaporation and recrystallisation of the residue from ethanol, there are obtained 10.3 g. (38% of theory) ethyl 4-[(4-chlorophenyl)-methyl]-7-hydroxy-2H-1-benzopyran-2-one-3-carboxylate; m.p. 167°–169° C.

(b) By reaction of the product obtained according to (a) above with 3-{4-[(4-chlorophenyl)-methyl]-1-piperazinyl}-propyl chloride in a manner analogous to that described in Example 1, there is obtained the ethyl ester of the title compound in the form of the dihydrochloride; yield: 73% of theory; m.p. 228°–229° C., after recrystallisation from aqueous ethanol.

(c) The title compound is obtained by saponification of the ethyl ester obtained according to (b) above with a mixture of 2N aqueous sodium hydroxide solution and ethanol in a manner analogous to that described in Example 2. Yield of dihydrochloride: 65% of theory; m.p. 245°–248° C., after recrystallisation from aqueous acetone.

EXAMPLE 13

In a manner analogous to that described in Example 8, paragraph 1, from the appropriate carboxylic acids, by reaction with thionyl chloride in chloroform, there are obtained the following compounds:

(a) 7-{3-{4-[(4-chlorophenyl)-methyl]-1-piperazinyl}-propoxy}-4-phenylmethyl-2H-1-benzopyran-2-one-3-carboxylic acid chloride as the dihydrochloride: yield 92% of theory; m.p. 280°–283° C.

(b) 7-{3-{4-[(4-chlorophenyl)-methyl]-1-piperazinyl}-propoxy}-4-[(4-chlorophenyl)-methyl]-2H-1-benzopyran-2-one-3-carboxylic acid chloride as the dihydrochloride; yield 97% of theory; m.p. 277°–282° C.

EXAMPLE 14

In a manner analogous to that described in the variant (a) of Example 8, from the appropriate carboxylic acid chlorides there are prepared the following compounds:

(a) 7-{3-{4-[(4-chlorophenyl)-methyl]-1-piperazinyl}-propoxy}-4-phenylmethyl-2H-1-benzopyran-2-one-3-carboxylic acid amide as the dihydrochloride; m.p. 185°–189° C. The dihydrochloride monohydrate melts at 169°–173° C.; yield: 72% of theory.

(b) 7-{3-{4-[(4-chlorophenyl)-methyl]-1-piperazinyl}-propoxy}4-[(4chorophenyl)-methyl]-2H-1-benzopyran-2-one-3-carboxylic acid amide as the dihydrochloride; m p. 204°–207° C., after recrystallisation from aqueous acetone; yield: 69% of theory.

EXAMPLE 15

Tablets are prepared, each of which contains 10 mg. of the compound according to Example 1. The tablets are prepared according to the following formulations:

| | |
|---|---|
| compound of Example 1 | 10 g. |
| lactose | 80 g. |
| starch | 29 g. |
| magnesium stearate | 1 g. |

The compound of Example 1 is finely pulverised and mixed with the lactose and starch. The mixture is then granulated in conventional manner. The magnesium stearate is added to the granulate and the mixture then pressed to give 1000 tablets, each of which has a weight of 0.12 g.

It will be understood that the specification and examples are illustrative but not limitative of the present invention and that other embodiments within the spirit and scope of the invention will suggest themselves to those skilled in the art.

What is claimed is:

1. A 2H-1-Benzopyran-2-one compound of the formula:

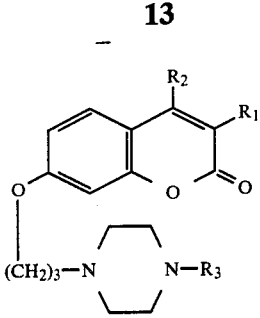

wherein
- R₁ is $C_1$–$C_6$ alkyl or $C_1$–$C_6$ alkyl substituted by phenyl or phenyl substituted by $C_1$–$C_6$ alkyl, $C_1$–$C_6$ alkoxy, hydroxyl, fluorine, chlorine or bromine and R₂ is trifluoromethyl, cyano, hydroxymethyl, $C_1$–$C_6$ alkoxymethyl, $C_1$–$C_6$ acyloxymethyl, halomethyl, aminomethyl, mono- or dialkylaminomethyl wherein each alkyl has 1–6 carbon atoms, $C_1$–$C_6$ acyl, carboxyl, $C_1$–$C_6$ alkoxycarbonyl or carbamoyl, which can be mono- or disubstituted by $C_1$–$C_6$ alkyl; or
- R₁ is trifluoromethyl, cyano, hydroxymethyl, $C_1$–$C_6$ alkoxymethyl, acyloxymethyl, halomethyl, aminomethyl, mono- or dialkylaminomethyl wherein each alkyl has 1–6 carbon atoms, $C_1$–$C_6$ acyl, carboxyl, $C_1$–$C_6$ alkoxycarbonyl or carbamoyl, which can be mono- or disubstituted by $C_1$–$C_6$ alkyl, and R₂ is a $C_1$–$C_6$ alkyl or $C_1$–$C_6$ alkyl substituted by phenyl or phenyl substituted by $C_1$–$C_6$ alkyl, $C_1$–$C_6$ alkoxy, hydroxyl, fluorine, chlorine or bromine and
- R₃ is phenyl, benzyl, or phenyl or benzyl substituted by $C_1$–$C_6$ alkyl, $C_1$–$C_6$ alkoxy, hydroxyl, fluorine, chlorine, or bromine; and the pharmacologically acceptable salts thereof.

2. The compound of claim 1 wherein
R₁ is $C_1$–$C_6$ alkyl or $C_1$–$C_6$ alkyl substituted by phenyl or phenyl substituted by $C_1$–$C_6$ alkyl, $C_1$–$C_6$ alkoxy, hydroxyl, fluorine, chlorine or bromine and R₂ is trifluoromethyl, cyano, hydroxymethyl, $C_1$–$C_6$ alkoxymethyl, $C_1$–$C_6$ acyloxymethyl, halomethyl, aminomethyl, mono- or dialkylaminomethyl wherein each alkyl has 1–6 carbon atoms, $C_1$–$C_6$ acyl, carboxyl, $C_1$–$C_6$ alkoxycarbonyl or carbamoyl, which can be mono- or disubstituted by $C_1$–$C_6$ alkyl.

3. The compound of claim 1 wherein
R₁ is trifluoromethyl, cyano, hydroxymethyl, $C_1$–$C_6$ alkoxymethyl, acyloxymethyl, halomethyl, aminomethyl, mono-or dialkylaminomethyl wherein each alkyl has 1–6 carbon atoms, $C_1$–$C_6$ acyl, carboxyl, $C_1$–$C_6$ alkoxycarbonyl or carbamoyl, which can be mono- or disubstituted by $C_1$–$C_6$ alkyl, and R₂ is a $C_1$–$C_6$ alkyl or $C_1$–$C_6$ alkyl substituted by phenyl or phenyl substituted by $C_1$–$C_6$ alkyl, $C_1$–$C_6$ alkoxy, hydroxyl, fluorine, chlorine or bromine.

4. The compound of claim 1 wherein each said alkyl is individually selected from the group consisting of methyl or ethyl and each said alkoxy group is individually selected from the group consisting of methoxy or ethoxy.

5. The compound of claim 1 wherein
R₁ is $C_1$–$C_6$ alkyl or $C_1$–$C_6$ alkyl substituted with phenyl,
R₂ is trifluoromethyl, cyano, hydroxymethyl, $C_1$–$C_6$ alkoxymethyl, carboxyl or N, N'-$C_1$–$C_6$-dialkyl-carbamoyl.

6. The compound of claim 1 wherein each said acyloxymethyl is benzoyloxymethyl, pivaloyloxymethyl or acetoxymethyl.

7. The compound of claim 1 designated 7-{3- {4-[(4-chlorophenyl)-methyl]-1-piperazinyl}- propoxy}-4-methyl-2H-1-benzopyran-2-one-3-carboxylic acid.

8. The compound of claim 1 designated 7-{3-{4-[(4-chlorophenyl)-methyl]-1-piperazinyl}-propoxy}-4-hydroxymethyl-3-methyl-2H-1-benzopyran-2-one.

9. The compound of claim 1 designated 7-{3-{4-[(4-chlorophenyl)methyl -1-piperazinyl}-propoxy}-3-cyano-4-methyl -2H-1-benzopyran-2-one.

10. The compound of claim 1 designated 7-{3-{4-[(4-chlorophenyl)-methyl]-1-piperazinyl}-propoxy}-4-methyl-2H-1-benzopyran-2-one-3-carboxylic acid diethylamide.

11. The compound of claim 1 designated 7-{3- {4-[(4-chlorophenyl)-methyl]-1-piperazinyl}-propoxy}-3-hydroxymethyl-4-methyl-2H-1-benzopyran-2-one.

12. A pharmaceutical composition comprising a therapeutically effective amount, for inhibiting allergic reactions of the skin and bronchi and inflammations, of the compound of claim 1 in a pharmaceutically acceptable carrier.

13. The pharmaceutical composition of claim 12 comprising 10 to 300 mg of said compound in a carrier suitable for oral ingestion.

14. The pharmaceutical composition of claim 12 comprising 0.05 to 50 mg/ml of said compound in a carrier suitable for injection.

15. A pharmaceutical composition comprising a therapeutically effective amount, for inhibiting allergic reactions of the skin and bronchi and inflammations, of thecompound of claim 1 designated
7-{3-{4-[(4-chlorophenyl)-methyl]-1-piperazinyl}-propoxy}-4-hydroxymethyl-3-methyl-2H-1-benzopyran-2-one
7-{3-{4-[(4-chlorophenyl)-methyl]-1-piperazinyl}-propoxy}-3-cyano-4-methyl-2H-1-benzopyran-2-one
7-{3-{4-[(4-chlorophenyl)-methyl]-1-piperazinyl}-propoxy}-4-methyl-2H-1-benzopyran-2-one-3-carboxylic acid diethylamide.
7-{3-{4-[(4-chlorophenyl)-methyl]-1-piperazinyl}-propoxy}-3-hydroxymethyl-4-methyl-2H-1-benzopyran-2-one   7-{3-{4-[(4-chlorophenyl)-methyl)]-1-piperazinyl}-propoxy}-4-methyl-2H-1-benzopyran-2-one-3-carboxylic acid
in a pharmaceutically effective carrier.

16. A method of inhibiting allergic reactions of the skin and bronchi comprising administering, orally or by injection, an effective amount of the compound of claim 1.

17. A method of inhibiting allergic reactions of the skin comprising applying to the skin, an effective amount of the compound of claim 1.

* * * * *